United States Patent [19]
Watson et al.

[11] Patent Number: 5,688,486
[45] Date of Patent: Nov. 18, 1997

[54] USE OF FULLERENES IN DIAGNOSTIC AND/OR THERAPEUTIC AGENTS

[75] Inventors: Alan D. Watson, Campbell, Calif.; Jo Klaveness, Oslo, Norway; Gene C. Jamieson, Boulder Creek; Jere D. Fellmann, Livermore, both of Calif.; Nils B. Vogt, Oslo, Norway

[73] Assignee: Nycomed Salutar, Inc., Sunnyvale, Calif.

[21] Appl. No.: 284,606

[22] PCT Filed: Feb. 11, 1993

[86] PCT No.: PCT/GB93/00279
§ 371 Date: Oct. 31, 1994
§ 102(e) Date: Oct. 31, 1994

[87] PCT Pub. No.: WO93/15768
PCT Pub. Date: Aug. 19, 1993

[30] Foreign Application Priority Data

Feb. 11, 1992 [GB] United Kingdom ................ 9203037

[51] Int. Cl.$^6$ .................................................. A61K 51/00
[52] U.S. Cl. .................... 424/1.65; 424/9.36; 424/9.42
[58] Field of Search ............................. 424/1.65, 1.85, 424/1.89, 9.36, 9.42, 9.5, 9.1; 423/263, 445; 570/130; 534/15

[56] References Cited

U.S. PATENT DOCUMENTS 5,177,248  1/1993  Chiang et al. .................... 560/86
5,248,498  9/1993  Neumann et al. .................... 424/9

Primary Examiner—James J. Seidleck
Assistant Examiner—Michael A. Williamson
Attorney, Agent, or Firm—Fish & Richardson P.C.

[57] ABSTRACT

Compounds including tight molecular meshes, preferably curved in one or two directions, such as fullerenes and met-cars, can be used as carriers for diagnostic or therapeutic agents, especially diagnostic contrast agents.

35 Claims, No Drawings

USE OF FULLERENES IN DIAGNOSTIC AND/OR THERAPEUTIC AGENTS

This application is 371 of PCT/GB93/00279 filed on Feb. 11, 1993.

BACKGROUND OF THE INVENTION

This invention relates to the use of macromolecular compounds having tight molecular meshes, for example non-diamond carbon allotropes and in particular carbon-based macromolecular structures such as fullerenes, graphite and amorphous carbons, as therapeutic or diagnostic agents, in particular as contrast enhancing agents for contrast media for diagnostic imaging procedures, especially magnetic resonance imaging (MRI), magnetometric imaging (MSI), electrical impedance tomography (EIT), X-ray, ultrasound and scintigraphy.

Contrast agents may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging the contrast agents function by modifying the X-ray absorption characteristics of the body sites in which they distribute; magnetic resonance contrast agents generally function by modifying the density or the characteristic relaxation times $T_1$, $T_2$ and $T_2^*$ of the nuclei, generally water protons, from the resonance signals of which the images are generated; scintigraphic contrast agents (a term used herein to include PET contrast agents) act as emitters of detectable radiation; and magnetometric contrast agents act by creating perturbations in the magnetic field in the body zones into which they distribute, perturbations which can be detected for example by SQUID magnetometers; and ultrasound contrast agents function by modifying the speed of sound or the density in the body sites into which they distribute.

The X-ray contrast agents first developed, barium sulfate and sodium iodide, have been superseded by iodinated organic compounds, in particular triiodophenyl compounds. Proposals have also been made to utilize the X-ray absorption properties of the lanthanides and other high atomic number metals to develop contrast agents with improved X-ray attenuation especially at the wavelengths used in CT; however these attempts have generally been relatively unsuccessful.

Thus, for example, Nalbandian et al. (see Ann. N. Y. Acad. Sci. 78: 779 (1959)) and Shapiro et al. (see Ann. N. Y. Acad. Sci. 78: 756 (1959)) proposed the use of the diethylenetri-aminepentaacetic acid (DTPA) chelate of bismuth (BiDTPA) and the ethylenediaminetetraacetic acid (EDTA) chelate of lead (PbEDTA) as radiographic contrast agents but encountered problems of solubility and toxicity. In U.S. Pat. No. 4,176,173 Winchell et al. described the use of simple hafnium or tantalum complexes as X-ray contrast agents and more recently, ytterbium DTPA has been studied as an intravascular X-ray contrast agent, and an $LD_{50}$ of 10 mmoles/kg has been reported (see Unger et al. Invest. Radiol. 21: 802 (1986)).

In MRI, the use of paramagnetic metal ions, such as $Mn(II)$, as contrast agents was first proposed by Lauterbur et al. in 1978 (see pages 752–759 in "Electrons to Tissues—Frontiers of Biological Energetics" Vol. 1, edited by Dutton et al., Academic Press, New York, 1978) and since that time a wide range of paramagnetic metal ion chelate complexes have been proposed for use in MRI. Thus for example Schering AG in U.S. Pat. No. 4,647,447 propose the use of salts of gadolinium(III) chelates of DTPA. More recently the use of superparamagnetic particles as MRI contrast agents has been described by Jacobsen in U.S. Pat. No. 4,863,715.

Whilst metal chelate contrast agents are used in MRI, they are not directly suitable for all applications (e.g. visualisation of certain body areas such as the gastrointestinal (GI) tract) and in certain cases concerns exist regarding their stability and side effects. Attempts have been made to achieve tissue-specific MRI contrast enhancement or to enhance stability and/or relaxivity by coupling of the paramagnetic chelates, or metal complexing groups, to various macromolecules or biomolecules such as polysaccharides, proteins, antibodies or liposomes—see for example EP-A-130934 (Schering), EP-A-136812 (Technicare), EP-A-184899 (Nycomed), EP-A-186947 (Nycomed), EP-A-277088 (Schering), EP-A-305320 (Schering), WO-A-88/07521 (Schering), WO-A-88/08422 (Schering), WO-A-85/05554 (Amersham), WO-A-89/06979 (Nycomed), EP-A-331616 (Schering) and Schmiedl et al. Radiology 162:205 (1987).

Nonetheless there still remains a need for contrast agents having improved properties, e.g. in terms of contrast enhancement, biodistribution, stability, opacity, relaxivity, tolerability, etc.

Similarly in the field of therapeutics there has long existed a need for the targetting of therapeutically active entities, such as molecules, ions, etc.

SUMMARY OF THE INVENTION

Viewed from one aspect the present invention therefore provides the use of a molecular mesh non-diamond carbon allotrope, or a chemically analogous structure, for the preparation of a diagnostic or therapeutic agent, e.g. a diagnostic imaging contrast medium.

As diagnostic agents, the molecular mesh compounds may be used as contrast enhancing agents in imaging modalities such as MRI, ultrasound, PET, Overhauser MRI, scintigraphy, X-ray CT, SPECT, magnetometric tomography, EIT, visible and ir imaging and as carriers for signal reporters (e.g. chromophores or fluorophores or radiolabels) optionally attached to biomolecules. Besides use in vivo, the mesh compounds can be used in in vitro diagnostic procedures such as assays and tissue staining. In such procedures, the mesh compounds are particularly suitably the carriers for a signal forming entity, e.g. a chromophore, fluorophore, radiolabel, magnetic label, an entity having a prominent characteristic radiation absorption maximum, etc. As therapeutic agents, the molecular mesh compounds, e.g. tubular or cage structures, may be used to carry and release therapeutically active molecules or atoms or in photodynamic therapy or radiotherapy or to function themselves as therapeutic agents and again may be conjugated to biomolecules to produce therapeutic bioconjugates.

The present invention resides in the realization that carbon allotropes (other than diamond which is excluded by reason both of cost and its physicochemical properties) and other analogous reticulate molecular structures may be used as a basic structural component for diagnostic or therapeutic agents, e.g. contrast agents, serving as the diagnostic entity itself or as carriers, targetting agents for diagnostic or therapeutic entities or as the active entity itself. The diagnostic or therapeutic entities or moieties as referred to herein may be atoms, ions, molecules, radicals, voids, clusters or particles or the like which of themselves have therapeutic or contrast enhancing properties, e.g. electromagnetic and radiation absorbing, reflecting or emitting properties.

Thus viewed from another aspect the invention provides a physiologically tolerable compound comprising a planar or more preferably a curved mesh-like molecular structure in the skeleton of which essentially all the mesh aperture ring atoms are branching sites, or a conjugate, intercalate, inclusion compound or salt thereof, for use as a diagnostic or therapeutic agent, with the proviso that where said compound is a carbon allotrope said mesh-like structure is curved in at least one direction.

While the use of carbon as a therapeutic agent, e.g. in oral treatment to reduce the effects of alcohol or other poisons, is known and as a result a proviso is set out in the foregoing paragraph, the use of carbon mesh materials as diagnostic agents and the use of curved mesh carbon materials as therapeutic agents is new.

Besides carbon, other materials form reticulate structures of the type defined above. These include for example compounds such as boron nitride and tungsten sulphide where the skeleton is carbon-free as well as other compounds such as boron hydrides, carboranes the so-called metallo-carbohedranes or met-cars in which the mesh framework is part carbon atoms and part metal atoms. Generally the rings of the skeleton (the holes in the net) are five or six membered. Where the mesh-like structure is curved in two dimensions to produce a closed cage the cage skeleton will usually require at least 20 atoms.

The non-diamond carbon allotropes useful according to the invention include the long known graphite and amorphous carbons but preferably are the more recently discovered or developed macromolecular forms where instead of having a planar laminar structure like graphite the carbon web is curved in one or more directions to produce a fullerene, having for example tubular or cage-like conformations. Closed cage fullerenes have been given the informal name "buckyballs" while the tubular structures have by analogy been called "buckytubes".

These macromolecular carbon allotropes are especially preferably used according to the invention as supports or surrounds for diagnostic or therapeutic entities, e.g. atoms, ions, free radicals, molecules or complexes or other entities the physicochemical properties of which enable them to exert a therapeutic effect or to function as contrast agents in a selected imaging modality. These will be discussed further below but it will be evident that therapeutically effective metals (e.g. vanadium, palladium, radioisotopes etc.) may exert their therapeutic effect optionally after release, for example from within a tubular mesh or from between the layers of a lamellar structure, paramagnetic metal atoms or ions and complexes thereof as well as paramagnetic molecules or free radicals may function as MRI contrast agents, radioisotopes may function as scintigraphic contrast agents or radiotherapeutic agents and heavy elements or ions or compounds or complexes thereof may function as X-ray contrast agents.

In certain imaging modalities the macromolecular mesh may itself function as a contrast agent and this and the use of the mesh itself as a therapeutic agent are included within the scope of the invention.

Where a diagnostic or therapeutic entity is to be carried by the mesh structure, this may be achieved in at least four ways: skeleton atoms in the mesh structure (e.g. carbon atoms in a carbon allotrope) may be derivatised to bind the diagnostic or therapeutic entity directly or indirectly to the skeleton; diagnostically or therapeutically effective atoms may be substituted for framework atoms (as for example in the boron-doped fullerenes and the met-cars); the diagnostic or therapeutic entity may be intercalated between adjacent webs (as for example in graphite, a buckytube or an amorphous carbon); or the diagnostic or therapeutic entity may be entrapped within a cage-like mesh (as for example within a buckyball). Moreover in each case the skeleton may be derivatised to enhance other properties of the macromolecule, e.g. to include hydrophilic or lipophilic groups or biologically targetting groups or structures. Examples of macromolecules, biomolecules and macrostructures to which the mesh structure may be conjugated in this regard include polymers (such as polylysine or polyethyleneglycol), dendrimers (such as 1st to 6th generation starburst dendrimers, in particular PAMAM dendrimers), polysaccharides, proteins, antibodies or fragments thereof (especially monoclonal antibodies and fragments such as Fab fragments thereof), glycoproteins, proteoglycans, liposomes, aerogels, peptides, hormones, steroids, microorganisms, human or non-human cells or cell fragments, cell adhesion molecules (in particular nerve adhesion molecules such as are described in WO-A-92/04916), other biomolecules, etc.) to assist in the achievement of a desired biodistribution. Generally, such derivatization will most conveniently be achieved by introduction of amine or hydroxyl functions to which the macromolecule, biomolecule, etc can be bound either directly or via a linker molecule, e.g. a bi or polyfunctional acid, activated acid or oxirane.

Non-diamond allotropic carbons and its analogues such as boron nitride have generally been thought of as very stable. While this is true physically, these structures readily lend themselves to surface modification by chemical means and the opportunities for selective derivatization are very rich. Indeed many carbon allotropes are produced or occur naturally in derivatized forms; this is particularly true for amorphous carbons and some soots and recently the natural occurrence of fullerenes in rock has been reported (see Buseck, Science 257:215–217 (1992)).

Turning back to the basic macromolecular structures, the form most preferred for use according to the present invention is the carbon or part-carbon cage web curved in one or two dimensions to form tubes or cages, e.g. the fullerene class of molecules often referred to as buckyballs or buckytubes which have recently received much attention in the technical literature.

Fullerenes, or buckyballs, are notable for their hollow polyhedral shape and their stability. The most intensively studied such carbon molecule in this class is the $C_{60}$ carbon cluster buckminsterfullerene in which all 60 atoms are equivalent and lie at the apices of a truncated icosahedron— the perfect soccer ball shape. $C_{60}$ and its discovery are described extensively in the literature—see for example Kroto et al., Nature 318: 162 (1985); Kroto, Science 242: 1139 (1988); Curl and Smalley, Science 242: 1017–1022 (1988); Kroto, Pure and Applied Chem. 62: 407–415 (1990). Many other fullerenes having stable closed cage structures have been described, e.g. $C_{28}$, $C_{32}$, $C_{50}$, $C_{70}$ (the most predominant after $C_{60}$), $C_{82}$ and the so-called "giant" fullerenes $C_{240}$, $C_{540}$ and $C_{960}$ (see for example Kroto (1990) Supra). The production of nested carbon nanotubes has been described for example by Iijima et al. in Nature 354:56 (1991) and 356:776 (1992) and Ebbesen et al. in Nature 358:220 (1992).

Procedures for producing fullerenes in macroscopic (multigram) quantities using electric-arc graphite decomposition are now well known and published in the literature (see Kratschmer et al., Nature 347–354 (1990); Kosh et al., J. Org. Chem. 56: 4543–4545 (1991); Scrivens et al. JACS 114:7917–7919 (1992); and Bhyrappa et al. JCS Chem Comm 936–937 (1992)).

Fullerenes (or fullerene mixtures consisting primarily of $C_{60}$ and $C_{70}$) are also commercially available (MER Corp., Tucson, Ariz.; Texas Fullerene Corp., Aldrich; Strem Chemicals, Newburyport, Mass., etc.).

DETAILED DESCRIPTION

The fullerene carbon cages may be used according to the invention to enclose a diagnostic or therapeutic entity, e.g. a metal atom or ion, preferably one that is paramagnetic or is a radioisotope or one which has a large X-ray cross section, or they may be used as macromolecular carriers for externally bound such entities.

The entrapment of metals within fullerene cages, especially for $M@C_{60}$, $M@C_{82}$ and $M_2@C_{80}$ compounds, has been reported within recent years (see for example references to La @ $C_{44}$, La @ $C_{60}$, $La_2$ @ $C_{66}$, La @ $C_{82}$, Gd @ $C_{82}$, $La_2$ @ $C_{82}$, $Sc_3$ @ $C_{82}$, $La_3$ @ $C_{88}$, $La_4$ @ $C_{110}$, $La_3$ @ $C_{112}$, Y @ $C_{60}$, Y @ $C_{82}$ etc. by Heath et al JACS 107: 7779 (1985), Baum et al C&EN Sep. 2, 1991, pages 6–7, Baum, C&EN Dec. 16 1991, pages 17–20, Baum, C&EN Oct. 21 1991, pages 5–6, Curl et al Scientific American October 1991, pages 32–41, Johnson et al. Nature 355: 239–240 (1992), Chai et al. "Fullerenes with metals inside" J. Phys. Chem (1992) (see Bucky News Service @ #87— describes La @ $C_n$ where n=60, 70, 74, 82), Weiss et al JACS 110: 4464–4465 (1988), Baum C&EN 37–38 (27 Apr. 1992) and Laasonen et al. Science 258:1916–1918 (1992)). Examples of $M_n$ @ $C_m$ where M is Ce, Nd, Sm, Eu, Gd, Tb, Dy, Ho, Er, La, Sc, Y and Fe are referred to by Gillan et al. in J Phys Chem 96:6869–6871 (1992).

The use of $M_n$ @ $C_m$ (where m and n are positive integers and M is a metal), and especially M @ $C_{82}$ and $M_2$ @ $C_{80}$, compounds and their derivatives is particularly preferred according to the invention. This is especially the case where the entrapped metal results in the cage compound having magnetic, electrical conductance or X-ray attenuation properties detectable in MRI, MSI, EIT or X-ray CT.

Also produced with the nanotubes referred to above are a variety of polyhedral carbon nanoparticles having internal cavities (see Ruoff et al. Science 259:346–348 (1993)) which can be loaded with particles of a therapeutically or diagnostically effective material, e.g. by generating the particles from graphite packed with a metal oxide.

By way of explanation the nomenclature system now finding favour for cage-like mesh structures uses the symbol @ to designate the cage with the framework atoms to the right of the symbol and the cage-enclosed atoms to the left. Thus $Gd@C_{82}$ has a $C_{82}$ cage enclosing one gadolinium while $@C_{58}B_2$ has a $C_{58}B_2$ cage.

The cage structures useful according to the invention can entrap mono or polyatomic species within the cage (e.g. metals, metal compounds, alloys, gases, etc.); mono or polyatomic species can be covalently bonded to the framework atoms of the cage (e.g. halogen atoms, reactive groups, hydrophilic groups, lipophilic groups, chelant moieties, linker moieties, etc); and the framework atoms need not, as described above, all be the same element. As a result diagnostically or therapeutically effective entities may be incorporated into the cage structure based compounds in a variety of ways. Thus in a preferred aspect as the cage compounds of the present invention are used compounds of formula I

(I)

(where n and n' are zero or positive integers; m is an integer having a value of at least 20; $@R_{3_m}$ is a closed curved met-car, fullerene, or faux-fullerene or fulleroid formed from m mesh aperture ring atoms $R_3$ which may be the same or different; each $R_2$ which may be the same or different is a mono or polyatomic species entrapped within the $@R_{3_m}$ cage; and each $R_4$ which may be the same or different is a mono or polyatomic species covalently bound to the $@R_{3_m}$ cage) and the salts thereof, especially those with physiologically compatible counterions, such as those conventionally used in the pharmaceutical art.

In formula I, the upper limit for m corresponds to that for stable cage compounds and may be many thousands. However, for the non-nested cages m will generally lie in the range 20–5000, e.g. 28 to 1000, especially 44 to 116, particularly 60 to 90. m will generally be an even number. The upper limits for n and n' are determined by the cage size, i.e. by m. n will generally be from 0 to 5000 for the non-nested structures and conveniently will be 0 to 10, especially 0 to 4. n' is simply limited by the number of attachment sites on the cage framework and by the bulk of the attached $R_4$ entity. Typically n' may be up to 60, e.g. 0 to 30.

This surface modification of cage structures such as fullerenes, for example to enable attachment of groups which can be used to complex diagnostic or therapeutic entities or which themselves are diagnostic or therapeutic entities, has received much attention recently.

Thus for example fullerenes are known to form anions on reduction with various reducing agents, e.g. lithium in THF (see Bausch et al JACS 113: 3205 (1991)), to produce polyanions ($C_n^-$) which can readily be alkylated, e.g. by reaction with alkyl halides. Similarly fullerenes can be polyhalogenated, e.g. by reaction with fluorine, chlorine or bromine (see Olah et al JACS 113: 9385–9387 (1991), Selig et al JACS 113: 5475–5476 (1991) and Birkett et al. Nature 357:479–481 (1992)) and the polyhalides ($C_n Hal_m$, where n and m are positive integers and Hal is a halogen atom such as F, Cl Br and I) may readily be alkoxylated or arylated, e.g. by reaction with an alkanol under basic conditions or by a Friedel-Crafts reaction with an aromatic compound and aluminium chloride. The preparation of iodinated fullerenes is discussed by Ohno et al. Nature 1992 "Doping of $C_{60}$ with iodine" (see Bucky News Service @ #211). The preparation of positively charged, water soluble fullerenes is described in J Phys Chem 96:5231 (1992).

Moreover fullerenes may be treated with a range of nucleophiles to yield adducts, e.g. of primary or secondary amines, dienes etc. (see Hirsch et al in Large Carbon Clusters, ACS Symposium Series 1991 and in Angew. Chem. Int. Ed. Engl. 30: 1308–1310 (1991) and Stry et al. JACS 114:7914–7916 (1992)). Several other surface modification reactions of fullerenes to produce compounds with groups covalently bound or complexed to the carbon skeleton have been described in the literature (see for example Hawkins et al Science 252: 312–313 (1991), Fagan et al Science 252: 1160–1161 (1991) and JACS 114:9697–9699 (1992), Penicaud et al JACS 113: 6698–6700 (1991), Pykett Nature 351: 602–603 (1991), Baum C&EN Dec. 16, 1991, pages 17–20, Zhang et al Nature 353: 333–335 (1991), Allemand et al Science 253: 301–303 (1991) and Fagan et al. Chapter 12 in "Fullerenes" ACS Symposium Series No. 481, 1992).

Conjugation of fullerenes to saccharides similarly offers an attractive route to achieving desired biodistribution for the macromolecular cages. In this regard, the production of C₆₀ glycosides has been reported by Vassella et al. in Angew Chem Int Eng. Ed 31:1388–1390 (1992). The conjugation of fullerenes to biotargetting proteins (e.g. asialoglycoprotein) can be achieved for example by the use of a linker molecule such as polylysine which is first conjugated to the fullerene, e.g. as described in the Examples below.

A further modification of the cage-compounds which is of particular interest for their therapeutic or diagnostic use according to the invention is their loading into carrier species, e.g. so as to increase their solubility and/or biotolerability. Thus for example fullerenes may be loaded into cyclodextrins using the procedure of Andersson et al. (JCS Chem Comm 604–606 (1992)) to yield a water soluble product that, as may be seen from the Examples below, retains its diagnostic efficacy. Substituted, skeleton-doped or filled fullerenes or met-cars may be handled analogously.

One particularly interesting set of surface reactions described for fullerenes is that of stable radical formation; this is of especial interest since the paramagnetic properties of the radicals make them suitable candidates for use as MRI contrast agents both in conventional MRI and in Overhauser MRI (see Leunbach, EP-A-296833). The production of fullerene based radicals has been described by Krusic et al in Science 254: 1183–1185 (1991).

Where fullerenes are being used to entrap a diagnostic or therapeutic entity, e.g. a lanthanide ion, it is possible to "shrink-wrap" the entrapped species by exposing the cage complex to laser irradiation to cause repeated controlled $C_2$ expulsions. (See for example Smalley, "Doping the fullerenes", Chapter 10 in "Fullerenes", ACS Symposium Series No. 481, 1992 and the references listed therein). This is especially attractive for the production of MRI and magnetographic contrast agents as the electronic structure of the entrapped species will be caused to interact more extensively with the delocalized electron structure of the fullerene and/or with the molecules of the ambient fluid.

A further interesting set of fullerene derivatives for use as contrast agents includes those in which a chelating moiety is attached to the carbon surface, e.g. using the alkylation or alkoxylation procedures disclosed above. Such moieties, generally residues of aminopolycarboxylic acids or amide or ester derivatives thereof, may be used to chelate metal ion diagnostic entities, e.g. paramagnetic, radioactive or heavy metal species and the carbon skeleton can thus serve as the carrier for relatively large numbers (e.g. up to 30 or more) of such chelating groups and chelated species. The chelant groups, for example DOTA, DTPA, DO3A, TETA and dimers, trimers and oligomers thereof and other such compounds discussed in the MRI contrast agent patent applications of Nycomed, Schering, Salutar, Squibb, Bracco, Mallinckrodt, Guerbet and Celltech listed herein or referred to in patent applications listed herein (in particular EP-A-299795, EP-A-71564, EP-A-255471, WO-A-86/02841, EP-A-287465, WO-A-90/12598, EP-A-290047, WO-A-89/11868, WO-A-89/01476, EP-A-232751, EP-A-292689, EP-A-434345 and WO-A-89/05802), may conveniently be linked by alkylene chains attached either to their own carbon backbones or to one of the heteroatoms, e.g. as in

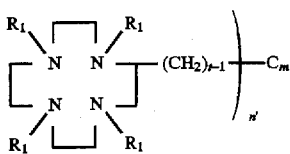

or

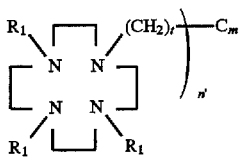

(where m, n' and t are integers, X is a linker group (e.g. a $C_{1-10}$alkylene chain optionally interrupted by an aryl group) and R is a $CH_2COOH$ group or a hydroxylated $C_{1-6}$alkyl group), a DO3A derivative which can be produced by reacting a DO3A-alkyl iodide with a fullerene. The linker group, shown as $(CH_2)_t$ above can of course optionally be substituted and linker groups such as are generally described in WO-A-91/05762, WO-A-90/12050, EP-A-305320, EP-A-255471 may be used. Similarly chelant attachment may be achieved by reaction of an amino adduct of a fullerene with a bifunctional linking group so that chelating groups, e.g. DOTA, DTPA, TACN etc. residues, can be attached. Such amine adducts might also be reacted with a free carboxyl group of a polycarboxylic acid chelant such as DTPA or DOTA or a free amine group in a chelant (e.g. a terminal amine group on a side chain, for example one attached to one of the heteroatoms of the backbone structure of the chelant) may be reacted directly with the fullerene to produce the amine adduct without requiring a separate linker group. Similarly, such free amine groups on chelant or linker moieties may undergo amidation reactions with carboxyl, or activated carboxyl moieties bound to the fullerene surface.

Where amine adducts are used, it may be desirable to use deprotonation agents to remove overly labile protons, e.g. those α to the amine. Suitable agents include bases or alkoxides e.g. TMG, piperidine, tBuNH₃OH, NH₄OH pyridine, etc.

For such compounds, as for many of the carbon allotrope derivatives used according to the invention, it will be desirable to introduce solubilising groups, onto the carbon skeleton, or in or on the linker or chelate moieties. Examples of such solubilizing groups include keto, sulphoxo and polyether groups and also mono or polyhydroxylated and/or mono or polyalkoxylated alkyl or alkoxy groups. Thus polyiodinated and polybrominated fullerenes may be produced by metal catalysed metathesis of the polychlorinated fullerenes, e.g. using group VIII metal iodides such as NiI₂ or PdI₂. Partial replacement of the halides by unsaturated alkanols may be followed by oxidation to introduce hydrophilic surface groups. An example of such a reaction scheme is as follows:

$$C_{60} + 10\ Cl_2 \longrightarrow C_{60}Cl_{20}$$

$$C_{60}Cl_{20} + 10\ HO-CH_2-CH=CH_2 \xrightarrow{NaOH}$$

$$C_{60}Cl_{10}\ (OCH_2CH=CH_2)_{10}$$

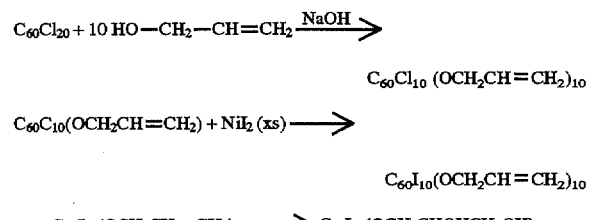

The iodine content of such compounds can be tailored to match or exceed those of conventional iodinated X-ray contrast agents while the increased molecular weights will give rise to different biodistribution patterns and excretion kinetics.

It is especially desirable to effect surface modification of the mesh structure, especially where this is a fullerene, to introduce hydroxy or amine functionalities (for example by the reaction schemes mentioned above or in the fullerene literature or by hydrolysis or ammoniolysis of halogen-containing materials) as this offers a route for the production of highly water-soluble products as well as providing reaction sites for further reaction to produce for example dimers, trimers, oligomers, polymers and bioconjugates. Such groups offer especially attractive reaction sites for ester or amide formation, e.g. by glucuronate formation, as for example in the preparation of ester or amide linked fullerene dimers, trimers etc. Similarly the introduction of hydrolysable groups such as linking or surface ester functions offers an attractive route to enhanced biodegradability.

Further opportunities for modification of molecular weights and loading capacities for diagnostic and therapeutic entities may be achieved by the use of bifunctional linkers, e.g. dihaloalkanes, to produce dimers, trimers or higher oligomers and in the limit polymers of the fullerenes. The oligomers can be derivatised as discussed above to provide chelating groups capable of complexing diagnostic metal ions or to introduce solubilising or other surface bound groups. Similarly a plurality of fullerenes, optionally derivatised, may be conjugated to a backbone, e.g. polymer, molecule (for example a polylysine or a starburst dendrimer) and if desired such a multiply fullerene loaded molecule can then be conjugated to a targetting molecule, e.g. a biomolecule as discussed above. Examples of backbone structures are discussed in WO-A-90/12050.

Dendrimers based on fullerenes, or other closed cage mesh structures such as the met-cars are particularly attractive compounds for use according to the invention. These can take three preferred forms: firstly where the mesh-structure is conjugated to a dendrimer which may carry other therapeutic or diagnostically effective groups at its other termini; secondly where an activated mesh structure is used as the core for the dendrimer (analogously to the use of a trifunctional molecule as the core in the preparation of PAMAM starburst dendrimers) which can carry desired therapeutically or diagnostically effective groups at its termini; and thirdly where activated mesh structures, e.g. activated fullerenes, are used as the dendrimeric branching sites and/or as the dendrimer termini thereby linking together a plurality of cage structures. These can be produced by standard dendrimer generation procedures, e.g. analogously to the procedures described by Tomalia and Nycomed Salutar in Angew Chem Int Ed Eng. 29:138 (1990), WO-A-88/01178, WO-A-90/12050 and PCT/EP92/02308 and the references cited therein, and may use other branching sites than carbon, e.g. as described in WO-A-90/12050.

Such cage structure, e.g. fullerene or met-car, dendrimers are novel and form a further aspect of the present invention. In this aspect the invention provides a dendrimer of formula II

(II)

where each Fu is a moiety of formula Ia

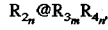
(Ia)

(where $R_2$, $@R_{3_m}$, n and n' are as defined above, and $R'_4$ is as defined above for $R_4$ or is a bond to an L moiety) linked to at least one linker moiety L; and x and y are integers each having a value of 1 to 100).

In formula II, the cage structure $@R_{3_m}$ is preferably a fullerene or a met-car, especially a fullerene and in particular $@C_{60}$. The entrapped species, where present, is preferably a metal, a metal compound, or a mixture of metals, especially heavy metals, transition metals and lanthanides. The covalently bound, non-L $R'_4$ groups are preferably either halogen atoms, cage activation groups (e.g. amine or hydroxyl groups or moieties containing such groups), chelant-moiety carrying groups, or lipophilic or hydrophilic or other biodistribution modifying groups. The linker moiety can be any suitable organic group such as those used in conventional dendrimers as discussed above. Where only one Fu group is present the linker moiety/moieties attached to it provide the dendrimeric structure. Where n is non-zero, cage filling may be effected during cage formation or subsequent thereto, e.g. using the electron beam evaporation technique of Ajayan et al. (see Nature 361:333 (1993)). This technique is especially attractive for use in the preparation of MRI, EIT or X-ray agents and in the case where entrappment of more than one metal element is desired and can be used for the preparation of compounds of formula I also.

Besides the "closed cage" fullerenes, one can also use more open carbon structures in accordance with the invention. Thus buckytubes (e.g. as discussed by Iijima (Supra) and Nature Nov. 7, 1991, page 56, Geake, New Scientist, Nov. 16, 1991, page 19, Ebbesen (supra) and Baum C&EN, Dec. 16 1991, pages 17–20) and graphite may act as the hosts for intercalated species which lie between adjacent carbon webs. Such species can include diagnostic or therapeutic entities as it is well known that various metals and chelating agents can be intercalated into the graphite structure. The introduction of paramagnetic metals and polyamine chelants to produce materials capable of functioning as MRI contrast agents is especially attractive. In this regard the technique of template formation of chelates in situ, such as has been done by Balkus et al (see for example Zeolites 10: 722–729 (1990) and J. Inclusion Phenom. 10: 141–151 (1991)) for zeolite-entrapped chelates is also especially attractive. The carbon skeleton might also be externally derivatised as discussed above for the closed cage structures.

The third category of carbon allotrope mentioned above was that of the amorphous carbons, including the soots. Amorphous carbon adsorbents are well known materials widely used in water, solvent and gas clean-up operations. The precise nature of amorphous carbons depends upon their source (e.g. oils, coals, woods, nut shells, bones and specific hydrocarbons) and subsequent treatment. Thus such carbons show a wide range of ion exchange, catalytic and sorbent properties and can have porous structures with pore sizes in the ranges conventional for zeolites and pillared clays. Some contain functional groups such as carboxyl, phenolic or nitrile groups which can be used directly for complexation of diagnostic metal ions or can be derivatised to achieve the desired properties, e.g. in terms of solubilising effect, complexing ability etc. The attachment of coordination complexes may be performed using techniques analogous to those used for conjugating such complexes to proteins or polymers and described at length in recent patent literature relating to MRI and X-ray contrast media. The complexes or chelating moieties which may be attached are analogous to those discussed above for the closed cage structures; thus for example one may use paramagnetic DOTA, DTPA or DO3A complexes and bifunctional linking agents.

Carbon attached or entrapped chelate complexes of heavy metal ions are particularly useful in diagnostic imaging or therapy. Especially preferred are metals of atomic numbers 20–32, 42–44, 49 and 57 to 83, especially Fe, Mn, Gd, Dy and Yb. For use as an MR-diagnostics contrast agent, the diagnostic entity is particularly suitably a paramagnetic species, conveniently a transition metal or lanthanide ion, preferably having an atomic number of 21–29, 42, 44 or 57–71. Eu, Gd, Dy, Ho, Cr, Mn or Fe are especially preferred and $Gd^{3+}$, $Mn^{2+}$ and $Dy^{3+}$ are particularly preferred.

For use as contrast agents in MRI, the paramagnetic metal species is conveniently non-radioactive as radioactivity is a characteristic which is neither required nor desirable for MR-diagnostic contrast agents. For use as X-ray or ultrasound contrast agents, the diagnostic entity is preferably a heavy atom such as I, W, Ta, Bi, Ba etc. or a compound or complex thereof, e.g. a chelated heavy metal species, for example a non-radioactive metal with an atomic number greater than 37, preferably greater than 50, e.g. W, Hf, Zr or Dy, for example $Dy^{3+}$. Multinuclear complexes, e.g. $W_3S_4$ TTHA, such as are described in WO-A-91/14460, might also be attached to the cage structures, e.g. after activation of the cage structure and the heavy metal complex.

This activation may be achieved by chelation of a multinuclear entity (e.g. a heavy metal complex cluster such as the $M_2$, $M_3$, $M_4$, etc clusters in WO-A-91/14460 and WO-A-92/17215 (where M is a metal, preferably a heavy metal such as W or Mo)) by a multidentate aminopolycarboxylic acid chelant (APCA), backbone derivatised to provide a functional group for attachment directly or indirectly to the cage-structure, e.g. to the polyamine moiety in a fullerene-polyamine conjugate such as those described in the Examples below. The backbone derivatization of the chelant would conveniently involve introduction of a substituted aralkyl group to yield a backbone-polymer conjugatable chelant analogous to those proposed earlier by Meares et al. (see Anal Biochem 142:68 (1984), JACS 110:6266 (1988) and Acc Chem Res 17:202 (1984)). Suitable chelant skeletons include linear, branched and cyclic APCA's such as DOTA, EDTA, TTHA, DTPA, TACN and suitable backbone derivative groups include R—$C_6H_4$—$CH_2$— where R is NCS, $OCH_2COOH$ etc. Methods of producing such derivatised chelants are known and are described for example in EP-A-217577 (Frincke) and J Radiol Chem 53:327 (1979). By way of example TACN and TTHA derivatives suitable for use in this regard may be produced by the following schemes:

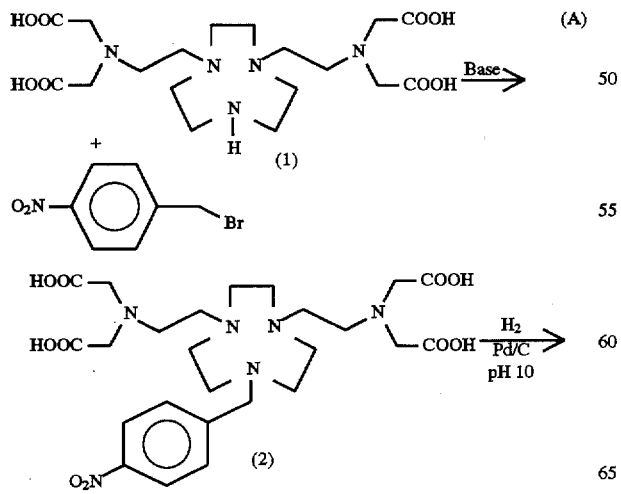

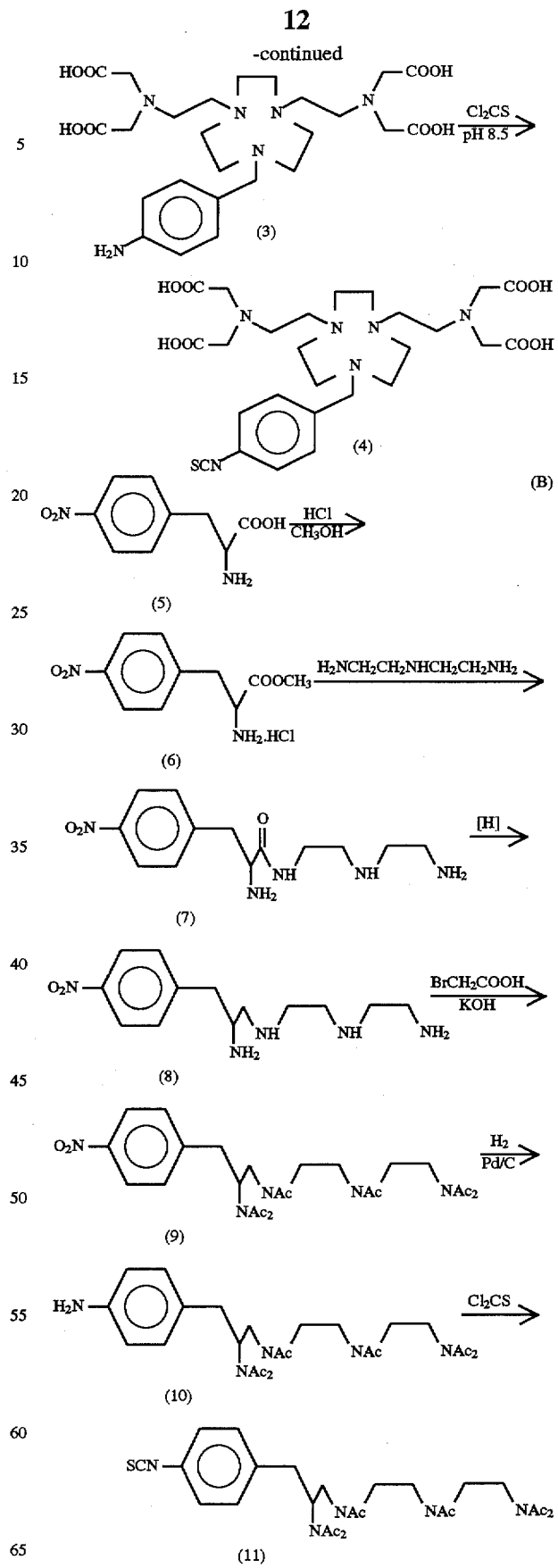

These functionalized metal cluster chelants can be coordinated to the metal cluster prior or subsequent to attachment to the cage structure or to a polymer, side chain or dendrimer attached thereto. Attachment is by standard synthetic procedures such as described in WO-A-90/12050 and the documents cited therein or by Meares et al. (Supra).

For use in scintigraphy, SPECT and radiotherapy, the diagnostic or therapeutic entity must of course be radioactive and conventional complexable radioactive metal isotopes, such as $^{99m}$Tc, $^{111}$In and $^{123}$I for example, will preferably be used. For radiotherapy, one may use chelated metals such as for example $^{153}$Sm, $^{67}$Cu or $^{90}$Y.

For use in PET, it will be especially preferred to use mesh structures in which some of the carbons are $^{11}$C and also to use $^{19}$F fluorinated carbon-mesh structures, especially fluorinated carbon allotropes, e.g. polyfluorinated buckyballs. $^{19}$F fluorinated carbon-mesh compounds will also be suitable for spectroscopy and spectroscopic imaging techniques as will $^{13}$C compounds. $^{19}$F fluorinated carbon-mesh compounds will also be especially suitable for use as MRI contrast agents in $^{19}$F imaging techniques. Polyfluorinated fullerenes are described for example by Selig et al. in JACS 113: 5475–5476 (1991).

Particles, such as the ferromagnetic or superparamagnetic particles of Jacobsen (supra), useful for MRI may also be bound to or entrapped within carbon structures according to the invention.

Many investigations are presently underway into the properties of fullerenes, and a number of modifications have been described. Thus a recent report has suggested that fullerene complexes may exhibit ferromagnetic properties in the absence of metal ions (Allem and et al., Science 253 301–303 1991). Such derivatised fullerenes exhibiting ferromagnetic or superparamagnetic properties may be used directly as diagnostic contrast agents according to the invention.

One property fullerenes have been found to possess is an electrical conductivity in solution which is light-sensitive (See U.S. Pat. No. 5,171,373) and accordingly these may be used as contrast agents in EIT where the site of interest is locally illuminated (e.g. via an optical fibre), or for photodynamic therapy (PDT) (see for example Zhu et al. Inorg Chem 31:3505 (1992)).

Where a paramagnetic metal containing carbon structure is to be used as an MRI contrast agent it is of generally important that the electromagnetic effects of the unpaired electrons should communicate to water molecules within or outside the structure.

As mentioned above, while the molecular meshes used according to the invention are preferably carbon meshes, other analogous molecular meshes may be used in which the carbon framework of the mesh is wholly or partially replaced by other atoms, as with the fulleroids and faux fullerenes, met-cars and boron-doped fullerenes, e.g. as in tungsten sulphide (see for example the publications of Reshef Tenne et al. of the Weizmann Institute of Science), molybdenum sulphide, boron nitride and the metallocarbohedranes.

Met-cars of various cage-sizes are known and have structures similar to those of the fullerenes. The met-car cage structures, @ $M'_{m_1}C_{m_2}$ (where $m_1$ and $m_2$ are positive integers and M' is a metal), are generally based on 5-membered rings and like the fullerenes there are distinct cage-sizes which show profound stability and as such are candidates for use as molecular meshes according to the invention. Thus stable single cage @ $M'_8C_{12}$ metallocarbohedrane compounds wherein M' is a transition metal (such as V, Zr, Hf, Ti etc.) are known (see Guo et al., Science 256:515–516 (1992) and Science 255:1411–1412 (1992) and Baum, C&EN 4–5 (16 Mar. 1992)). Multicage @ $M'_{13}C_{22}$, @ $M'_{14}C_{21}/_{23}$, @ $M'_{18}C_{29}$ and @ $M'_{22}C_{35}$ structures are also known (see Baum, C&EN 4–5 (11 May 1992)). Besides the inherent utility of such compounds as X-ray contrast agents, in view of their electronic properties (see Reddy et al. Science 258:1640–1643 (1992)) they are potential candidates for use as contrast agents in EIT. Moreover for use as MRI contrast agents, the analogous manganese compounds may be considered.

The met-cars may be derivatised to impart desired biodistribution properties, e.g. by surface attachment of hydrophilic groups or conjugation to biomolecules, as described above for the fullerenes.

Tungsten sulphide molecular meshes (as described for example by Tenne et al, in Nature 360:444–446 (1992)) are likewise attractive candidates for use as X-ray contrast agents due to the high X-ray cross section of tungsten.

Framework doped fullerenes, e.g. compounds $R_{2_n}@C_{m_2}X_{m_3}$ (where $m_2$ and $m_3$ are positive integers; X is a non-carbon, non-metal element such as boron (especially $^{10}$B); and $R_2$ is a metal or $R_{2_n}$ is a metal compound or alloy) may also be produced. In the case of the boron doped compounds, these and their derivatives may be used as therapeutic agents in neutron irradiation therapy, e.g. in anti-cancer treatment. The preparation of @$C_{60-x}B_x$ (where x is 1 to 6) is discussed for example by Smalley in Chapter 10 of "Fullerenes", ACS Symposium Series No. 481, 1992.

The mesh compounds according to the invention find diagnostic use for both in vivo and in vitro (or ex vivo) diagnostic procedures. Insofar as in vivo procedures are concerned, the imaging techniques discussed herein are of particular interest, in particular X-ray CT, MRI, MRS, OMRI, scintigraphy, PET, SPECT, light-imaging and ultrasound. However the meshes, in particular the curved meshes, also have potential for use in diagnostic assays and tissue staining procedures, e.g. as carriers of signal generating entities (e.g. radiolabels, chromophores, fluorophores, magnetic labels, etc) and of binding sites of whatever desired level of specificity, e.g. antibody fragments, adhesive glycoprotein fragments, boronic acid residues, etc.

As discussed above, the compounds are intended for use in therapy or diagnostics, e.g. diagnostic imaging and thus in a further aspect the invention also provides a composition, e.g. a diagnostic contrast medium, comprising a physiologically tolerable compound comprising a curved or planar mesh-like molecular structure in the skeleton of which essentially all ring atoms are branching sites and optionally carrying a diagnostic or therapeutic entity, and at least one pharmaceutically acceptable carrier, with the proviso that where said compound is graphite it carries a said diagnostic entity.

In a still further aspect, the invention provides a method of diagnostic imaging of a human or non-human animal (preferably mammalian) subject, said method comprising: administering to said subject a contrast agent comprising a physiologically tolerable compound comprising a curved or planar mesh-like molecular structure in the skeleton of which essentially all ring atoms are branching sites and optionally carrying a diagnostic entity; and generating an image of at least part of said subject, e.g. by X-ray imaging, EIT, MSI, PET, SPECT, scintigraphy or ultrasound but preferably by MRI, e.g. for encephalography.

Viewed from a yet still further aspect the invention provides a method of treatment of a condition responsive to radiation therapy, metal ion therapy, or photodynamic therapy, said method comprising administering to a subject a therapeutically effective amount of a physiologically tolerable compound comprising a curved or planar mesh-like molecular structure in the skeleton of which essentially all ring atoms are branching sites, said compound comprising at least one atom of a therapeutically effective element or isotope or being photoresponsive, and where appropriate exposing said subject to light at a site to which said compound distributes, i.e. light of the wavelength to which the compound is photoresponsive.

Besides the radioisotopes useful in radiotherapy, such as those mentioned hereinbefore, the mesh structure may thus be used to carry other therapeutically effective elements. These include metals such as platinum, ruthenium, rhodium, palladium, copper, vanadium, gold, calcium, manganese, lithium, chromium, zinc, iron, nickel, cobalt, silver and mercury as well as elements such as boron or cadmium having large neutron capture cross sections. The therapeutic effects of transition metals are discussed further by Farrell in "Transition metal complexes as drugs and therapeutic agents", Kluwer, 1989.

In general, in the methods of imaging and therapy according to the invention the therapeutic or diagnostic entities will be administered in doses approximately equal or somewhat less than those required for the conventional use of such entities in such methods.

For in vivo use, the diagnostic or therapeutic agents of the invention could be administered by any convenient route, e.g. iv, im, ip, or oral. When administration is into the circulatory system, the agent will preferably be presented as an ECF, blood pool or targetted agent. Normal factors, e.g. size, charge, target vector etc, can be used to produce the desired distribution. Thus for example high molecular weight (e.g. above 40 kD), soluble compounds are candidates for use as blood pool agents, and low molecular weight compounds are candidates for use as ECF agents.

The diagnostic or therapeutic agents of the present invention may be formulated with conventional pharmaceutical or veterinary formulation aids, for example stabilizers, antioxidants, osmolality adjusting agents, buffers, pH adjusting agents, etc. and may be in a form suitable for parenteral or enteral administration, for example injection or infusion or administration directly into a body cavity having an external escape duct, especially the gastrointestinal tract (e.g. by oral or rectal administration, for example as an orally ingestible suspension or as an enema), the bladder or the uterus. Thus the compositions of the present invention may be in conventional pharmaceutical administration forms such as tablets, capsules, powders, suspensions, dispersions, syrups, suppositories, etc; however suspensions and dispersions in physiologically acceptable carrier media, for example water or saline, will generally be preferred.

The agents according to the invention may therefore be formulated for administration using physiologically acceptable carriers or excipients in a manner fully within the skill of the art. For example, the macromolecular carbon, optionally with the addition of pharmaceutically acceptable excipients, may be suspended in an aqueous medium, with the resulting suspension then being sterilized. Suitable additives include, for example, physiologically biocompatible buffers (as for example, tromethamine hydrochloride), additions (e.g., 0.01 to 10 mole percent) of chelants (such as, for example, DTPA or DTPA-bisamide) or calcium chelate complexes (as for example calcium DTPA, CaNaDTPA-bisamide), or, optionally, additions (e.g. 1 to 50 mole percent) of calcium or sodium salts (for example, calcium chloride, calcium ascorbate, calcium gluconate or calcium lactate).

If the agents are to be formulated in suspension form, e.g. in water or physiological saline for oral administration, they may be mixed with one or more of the inactive ingredients traditionally present in oral solutions and/or surfactants and/or aromatics for flavouring. In this category mention may be made of salad oils, emulsifying agents, EZM carriers and barium compounds, all of which may be considered as carriers for products for oral GI use. Oral agents according to the invention may conveniently also be used in conjunction with clays, zeolites, superparamagnetic particles etc.

Particularly preferred components for the contrast media compositions also include gelling agents and in particular clays, for example smectite clays such as montmorillonite. The clays used can be diagmagnetic or paramagnetic (either naturally so or by ion exchange with paramagnetic cations). The weight ratios of such carbon structure: clay combinations will preferably be such that 1 part by weight carbon structure is combined with up to 100 parts by weight of clay.

Where a metal carrying carbon structure is to be used as a GI contrast agent, it should of course be in a form adequately stable for such use. Thus in the stomach the ambient pH is strongly acid while in the intestines the pH rises to near neutral and accordingly where the structure is acid sensitive it should be protected. Similarly for liver imaging it may be appropriate to encapsulate the carbon structures within liposomes or aerosomes or to attach them to the insides or outside of such vehicles.

The protecting of the carbon structure from the ambient body fluids can be approached in a variety of ways but the two most straightforward solutions are either by administration of the metal loaded carbon structure in a "delayed release" form (e.g. within capsules that disintegrate only after passage through the stomach or as a suspension formulated with a liquid buffering (and preferably also suspending) agent (e.g. EZpaque)) or by modification of the carbon skeleton to enhance its acid resistance.

For oral MRI contrast media it is of particular interest to provide a composition which can function effectively as a relaxation time and/or imaging nuclei density contrast medium, e.g. affecting one or more of $T_1, T_2, T_2^*$ and proton density, for example both $T_1$ and $T_2$. Compositions effective in this regard can be achieved by the combination of a paramagnetic metal-loaded carbon structure such as those discussed above with a further relaxation rate enhancing agent such as a particulate superparamagnetic, ferromagnetic or ferrimagnetic material, a clay (especially a smectite clay such as montmorillonite) or a fluorinated (preferably perfluorinated) agent, e.g. PFOB.

Fluorinated agents, metal oxides, especially ferrites, and other superparamagnetic, ferromagnetic and ferrimagnetic materials suitable for use in MRI contrast media, particularly media administrable into the GI tract are well known and have been widely discussed in the patent and technical literature, e.g. WO-A-89/11873 (Klaveness), EP-B-186616 (Gries), EP-A-368429 (Blaszkiewicz), U.S. Pat. No. 4,951,675 (Groman), and the documents cited therein.

Thus clays can perform a dual function in such combined media—as gelling agents and as relaxation agents. Similarly the perfluorinated agents such as PFOB can also perform not only as relaxation agents but also to increase the bowel transit time of the ingested contrast medium.

Accordingly, viewed from a further aspect, the invention provides an MRI contrast medium (composition) comprising a paramagnetic species carrying non-diamond carbon allotrope together with at least one relaxivity enhancing agent selected from the group consisting of physiologically tolerable clays, fluorinated organic compounds, ferromagnetic, ferrimagnetic and superparamagnetic particles, the magnetic particles optionally being carried or aggregated by a physiologically tolerable matrix material, said composition optionally further comprising at least one physiologically tolerable carrier or excipient.

For MRI and for X-ray imaging of some portions of the body the most preferred mode for administering the contrast agents is parenteral, e.g. intravenous, administration. Parenterally administrable forms, e.g. intravenous suspensions, should be sterile and free from physiologically unacceptable agents, and should have low osmolality to minimize irritation or other adverse effects upon administration, and thus the carrier medium should preferably be isotonic or slightly hypertonic. Suitable vehicles include aqueous vehicles customarily used for administering parenteral solutions such as Sodium Chloride Injection, Ringer's Injection, Lactated Ringer's Injection and other solutions such as are described in Remington's Pharmaceutical Sciences, 15th ed., Easton: Mack Publishing Co., pages 1405–1412 and 1461–1487 (1975) and The National Formulary XIV, 14th ed. Washington: American Pharmaceutical Association (1975). The suspensions can contain preservatives, antimicrobial agents, buffers and antioxidants conventionally used for parenteral solutions, excipients and other additives which are compatible with the carbon structures and which will not interfere with the manufacture, storage or use of the products.

Where the diagnostic agent comprises a toxic metal species, e.g. a heavy metal ion, it may be desirable to include within the formulation a slight excess of a chelating agent, e.g. as discussed by Schering in DE-A-3640708, or more preferably a slight excess of calcium, e.g. in the form of a Ca salt of such a chelating agent or another salt. For MR-diagnostic examination, the diagnostic agent of the present invention, if in suspension or dispersion form, will generally contain the diagnostic metal at concentrations in the range of micromole to 1.5 mole per liter, preferably 0.1 to 700 mM. The diagnostic agent may however be supplied in a more concentrated form for dilution prior to administration. The diagnostic agents of the invention may conveniently be administered in amounts of from $10^{-3}$ to 3 mmol of the diagnostic species per kilogram of body weight, e.g. about 0.1–1 mmol Gd/Kg bodyweight.

For X-ray examination, the dose of the contrast agent should generally be higher and for scintigraphic examination the dose should generally be lower than for MR examination.

The mesh compounds of the invention comprising a signal giving or modifying entity or a therapeutic entity (such as a heavy metal (detectable by X-ray), a magnetic label, a radiolabel, a fluorophore, a chromophore, a singlet oxygen generator, etc) may be incorporated into interventional medical apparatus, e.g. by coating onto or incorporation into the walls of a catheter, stent, angioplasty balloon etc. Thus in a further aspect the invention provides medical apparatus characterized in that at least a portion of the apparatus incorporates or is coated with a curved mesh structure compound comprising a signal forming or therapeutic entity selected from radiolabels, magnetic labels, elements of atomic number greater than 50, chromophores, fluorophores, and singlet oxygen generators.

The disclosures of all the documents mentioned herein are incorporated by reference.

The invention is illustrated further by the following non-limiting Examples:

EXAMPLE 1

$C_{60}$ $C_{60}$, buckminsterfullerene, is prepared and purified according to the procedures described by Kock et al. in J. Org. Chem. 56: 4543–4545 (1991). (Alternatively commercially available $C_{60}$, e.g. from Strem Chemicals, Newburyport, Mass., may be used in the syntheses described below).

EXAMPLE 2

$C_{60} F_{n'}$ (n'=30 to 60)

$C_{60}\,^{19}F_n$, e.g. for use as an MRI contrast agent, is prepared using the procedures described by Selig et al. in JACS 113: 5475–5476 (1991). For subsequent use as a PET contrast agent $^{18}F$ is used in the same procedures.

EXAMPLE 3

$Mt_n$ @ $C_m$ (Mt=lanthanide, transition or rare earth metal, m=60, 80, 82, 84, 92, 106 etc., and n=1, 2 etc.)

$Mt_n$ @ $C_m$ is prepared using procedures analogous to those described for La @ $C_{60}$ and La @ $C_{82}$ by Heath et al. in JACS 107: 7779–7780 (1985) and Johnson et al. in Nature 355: 239–240 (1992) and for $Ce_2$ @ $C_{80}$, Gd @ $C_{82}$, $Tb_2$ @$C_{84}$, $Ho_2$ @ $C_{84}$, $Tb_2$ @ $C_{92}$, $Ho_2$ @ $C_{106}$, Dy @ $C_{82}$, $Dy_2$ @ $C_{80}$ and $Dy_2$ @ $C_{84}$ using the procedures used by Gillan et al. J Phys Chem 96:6869 (1992). The lanthanide oxides $Gd_2O_3$ and $Dy_2O_3$ are substituted for the $La_2O_3$ used in the Johnson et al. procedure. The lanthanide halides $GdCl_3$ and $DyCl_3$ are substituted for the $LaCl_3$ used in the Heath et al. procedure. The paramagnetic cage complexes are useful as MRI contrast agents.

Certain metal, particularly lanthanum, iridium and lutecium, carbon-cage complexes can produce singlet oxygen when irradiated with appropriate wavelengths of light and therefore can be useful in photodynamic therapy.

EXAMPLE 4

$Cr(III)TPP(C_{60})$

The paramagnetic MRI contrast agent $Cr(III)TPP(C_{60})$ is produced by the procedures described by Penicaud et al. in JACS 113: 6698–6700 (1991).

EXAMPLE 5

$C_{60} I_{n'}$

Polyiodinated $C_{60}$ is prepared by reaction of polychlorinated $C_{60}$ (prepared according to the procedures of Olah et al. described in JACS 113: 9385–9387 (1991)) with an excess of nickel(II) iodide. The polyiodinated $C_{60}$ may be used as an X-ray contrast agent.

EXAMPLE 6

$C_{60}(CH_2C_6H_5)_{n'}$ (n'=3,5) radical

Tribenzyl (and pentabenzyl) buckminsterfullerene radicals are produced by reacting $C_{60}$ with photolytically generated benzyl radicals according to the procedure described by Krusic et al. in Science 254: 1183–1185 (1991). The radicals can be used as MRI contrast agents. For certain MRI modalities perdeuterated radical precursors may be used.

EXAMPLE 7

Conjugation of dodecylamino-$C_{60}$ to ASGP (asialoglycoprotein)

(a) Dodecylisothiocyanato-$C_{60}$

Dodecylamino-$C_{60}$ (20 mg; 0.022 mmol, prepared by the method of Wudl et al "Fullerenes", Chapter 11, page 168, ACS Symposium Series No. 481, 1992) is dissolved in $CHCl_3$ (1 mL) containing thiophosgene (5 µL, 7.5 mg, 0.06 mmol). $K_2CO_3$ (5 mg; 0.036 mmol) is added and the mixture is stirred under nitrogen for 1 h. The potassium salts are then filtered and the crude product precipitated with hexane (20 mL). The precipitate is then centrifuged, washed with hexane (twice) and then dried under vacuum.

The isothiocyanate derivatives of t-butylamino-$C_{60}$ and ethylenediamino-$C_{60}$ are prepared similarly employing the t-butylamino-$C_{60}$ and ethylenediamino-$C_{60}$ respectively as starting reagents.

(b) Conjugation of dodecylisothiocyanato-$C_{60}$ with ASGP

A solution of dodecylisothiocyanato-$C_{60}$ (5.4 mg; 0.006 mmol) in DMF (1 mL) is added in drops over 5 min to a solution of ASGP (26.4 mg; 0.6 µmol) in carbonate/bicarbonate buffer (0.1M, 15 mL) to avoid precipitation. After incubating at ambient temperature for 2h, the conjugate is purified by passage through Sephadex G-25 column (UV 254 nm detector), eluting with PBS buffer. (See Varadarajan et al. in Bioconj Chem 2:102–110 (1991)).

Dodecylisothiocyanato-$C_{60}$ can be conjugated to other proteins and antibodies analogously.

EXAMPLE 8

Conjugation of Polyamine-bound $C_{60}$ to ASGP (a) Attachment of dodecylisothiocyanato-$C_{60}$ polylysine A solution of dodecylisothiocyanato-$C_{60}$ prepared as in Example 7 above (150 mg; 0.17 mmol) in DMF (7 mL) is added dropwise to a solution of polylysine (37 mg, 1.7 mmol; degree of polymerization 103) in 7 ml bicarbonate buffer (0.1M, pH 8.1) and the solution is stirred at ambient temperature for 6h. The solution is passed through Sephadex G-25 column (UV 254 nm detector), eluting with PBS buffer to remove the small molecules. The eluate is then lyophilized. (See Sieving et al. in Bioconj Chem 1:65–71 (1991)).

The same procedure can be used to conjugate dodecylisothiocyanato-$C_{60}$ to other polyamines such as dendrimers (e.g. 2nd to 6th generation PAMAM dendrimers) or to conjugate other isothiocyanato-$C_{60}$ derivatives.

(b) $C_{60}$-polylysine activation

A solution of $C_{60}$-polylysine (100 mg) (Example 8(a)) in phosphate buffer (8 mM, pH 8.0, 9 mL) is treated dropwise with a solution of N-succinimidyl 4-(N-maleimidomethyl) cyclohexane-1-carboxylate (5 mg) in DMSO (1 mL), and stirred for 30 min. The reaction mixture is dialyzed against distilled water and lyophilized. The number of maleimido groups per polylysine molecule is assayed by Ellman's method.

The same method can be extended to other $C_{60}$-loaded polyamines such as dendrimers.

(c) ASGP activation

A solution of ASGP (26.4 mg; 0.6 µmol) in Ellman's buffer (15 mL; pH 8.36) is degassed under vacuum and cooled to 0° C. under a nitrogen atmosphere. A solution of 2-iminothiolane hydrochloride (13.4 mg; 0.097 mmol) in triethanolamine hydrochloride buffer (1 mM; pH 8.42; 0.6 mL) is added and the mixture stirred at 0° C. for 2 h. The solution is then dialyzed against phosphate buffer (0.08 mM phosphate containing 0.5 weight % EDTA; pH 7.8; 600 mL) overnight. The protein content in the dialysate is assayed by measurement of absorbance at 280 nm. The thiol content is assayed by Ellman's method. The number of thiol groups per ASGP is then calculated.

The same method can be extended to other proteins and antibodies.

(d) Conjugation of $C_{60}$-polylysine ASGP

A solution of activated $C_{60}$-polylysine (26 mg) in phosphate buffer (pH 8.0) is added to the activated ASGP solution and the mixture is stirred at ambient temperature for 4h. The mixture is then dialyzed against deionized water and purified by passage through Sephadex G-25 column (PBS eluent). The conjugate is then lyophilized.

EXAMPLE 9

Synthesis of water-soluble Gd@$C_{60}$ for use as an MRI Imaging Agent

Gd@$C_{60}$ is synthesized as described previously (see Example 3). The Gd@$C_{60}$ cluster is made water soluble using the method described by Chiang et al., J Am Chem Soc 114:10154–10157 (1992). In a 50 mL round bottom flask is placed 0.176 g (0.2 mmol) of Gd@$C_{60}$, nitronium tetrafluoroborate (8.0 mL, 4.0 mmol, 0.5M in sulfolane), benzoic acid (0.488 g, 4 mmol), and dichloromethane (20 mL). The reaction mixture is stirred under a nitrogen atmosphere for 2 days, after which the dichloromethane is removed by evaporation to afford a thick slurry. The slurry is slowly added to 50 mL of ice water, yielding an oil that solidifies on stirring. The solid is filtered and washed with hexane. After drying in air, 50 mg of the solid is weighed into a 25 mL flask; 10 mL of water and 150 mg of sodium hydroxide are added. The resulting mixture is heated for 8 hr with stirring. The resulting clear solution is concentrated to a volume of 5 mL and added to methanol, whereupon a precipitate of polyhydroxylated Gd@$C_{60}$ is obtained. The FAB mass spectrum shows peaks at m/z 878 (Gd@$C_{60}$), 894, 911, 927, 943, 961, and higher.

Gd@$C_{82}$ may be similarly derivatised.

EXAMPLE 10

Water-soluble Gd-imbedded fullerene for MRI imaging

Gd@$C_{60}$ is prepared as described by J. R. Heath et al., J Am Chem Soc, 107; 779 (1985), for La@$C_{60}$ as follows. A low-density graphite disk (Poco Graphite Inc., CZR-1 grade low density graphite, 1.54 g $cm^{-3}$) is impregnated with gadolinium by exposure over 24 hr to a boiling saturated solution of $GdCl_3$ in 10 ml water. After rinsing and drying, the disk is mounted in a rotation/translation device on the side of a pulsed supersonic nozzle. Vaporization is performed by 5 ns, 35 mJ pulses of a Nd:YAG laser at 532 nm focused to a 1 mm diameter spot on the graphite disk where the helium carrier (1 atm pressure) present in the pulsed nozzle at the time of laser vaporization thermalizes the carbon fragments ejected from the graphite surface and provides a buffer gas to stabilize the Gd-$C_n$ reaction products. Expansion of the cluster-laden gas then produces a supersonic beam which is probed 1.2 m downstream by a time-of-flight mass spectrometer. Ionization of the carbon clusters is produced by ArF excimer laser radiation at 6.4 eV. The TOF mass spectrum displays the Gd$C_{60}$ cluster in addition to other clusters. As described below, the Gd$C_{60}$ cluster, after separation, can be embedded in gamma-cyclodextrin to achieve water solubility according to the procedure used to similarly embed pure $C_{60}$ described by T Andersson et al., J Chem Soc Chem Commun. 604 (1992). The Gd@$C_{60}$ cluster (10 mg) is treated with an aqueous solution of gamma-cyclodextrin (2.6 g in 100 mL water) under reflux for 48 h. Any precipitate remaining after cooling to ambient temperature is removed by filtration to leave Gd@$C_{60}$ embedded in cyclodextrin in the solution. Similar results can be obtained using Dy, Ho, La, Lu, and other rare earth metals.

EXAMPLE 11

Synthesis and application of gas sorbents based on fullerenes for use as Ultrasound contrast agents $C_{60}$–$C_{70}$ mixtures are prepared as described by Kratschmer et al., Nature, 347: 354 (1990). The resulting material, after thorough drying, is exposed to hydrogen or oxygen gas. The initial pressure of the gas is observed to decrease, indicating adsorption or absorption of the gas. Repressurization of the gas is followed by subsequent pressure decreases until the $C_{60}$–$C_{70}$ mixture becomes saturated and does not sorb additional gas. Gas desorption is slow at ambient temperature, requiring 20 days or longer. Higher temperatures, agitation, and vacuum results in more rapid gas desorption (see also "Inside R&D", 21 (18), Apr. 29, 1992).

EXAMPLE 12

Synthesis of an osmylated fullerene useful for tissue staining

In the manner reported by Hawkins et al. (J Org Chem, 55:6250–6252 (1990)), a toluene solution of a 4:1 $C_{60}$–$C_{70}$ mixture and 2 equivalents of $OsO_4$ is reacted at 0° C. with 5 equivalents of pyridine. After 12 hours at ambient temperature, the resulting precipitate is filtered and washed with toluene to provide an 81% yield of osmate ester that analyzes correctly for the formula $C_{60}OsO_4(C_5H_5N)_2$. The infra red spectrum of this material shows absorption at 836 $cm^{-1}$ (assigned to the asymmetric $OsO_2$ stretch). This material is useful in staining tissues.

EXAMPLE 13

X-ray contrast agent based on $C_{60}$ molecules

[$(C_2H_5)_3P]_4$Pt (0.724 g, 1.08 mmol) is added to a solution of $C_{60}$ (75 mg, 0.10 mmol) in 5 ml of benzene, producing a dark orange-brown solution. After 10 min, the solvent and released triethlphosphine are removed in vacuo, and benzene is added until the compound redissolves. After filtration of a small amount of insoluble material, benzene is removed and hexane (6–10 mL) is added to the flask, resulting in the formation of an orange crystalline solid that is collected by filtration, washed three times with 1–2 mL portions of hexane, and dried in vacuo to afford an 88% yield of $\{[(C_2H_5)_3P]_2Pt\}_6C_{60}$. This material was found to be an effective X-ray contrast medium.

EXAMPLE 14

Sugar-labelled fullerenes for use in enzyme assays such as glucose oxidase

Sugar-labelled fullerenes are prepared as described by A. Vasella in Angew Chem Int Ed Engl, 31: 1388 (1992), followed by hydrogenolysis. A solution of $C_{60}$ (35 mg, 0.049 mmol) in 35 mL of toluene is treated with an O-benzyl protected diazirine monosaccharide (26.7 g, 0.049 mmol) under argon at 23° C. The solution is stirred for 3 h, the solvent is removed under vacuum, and the residue purified by flash chromatography ($SiO_2$, toluene) to yield 33 mg (55%) of O-benzyl-protected monoglycosylated $C_{60}$. The benzyl protecting groups can then be removed by hydrogenolysis. To O-benzyl-protected monoglycosylated $C_{60}$ (33 mg, 0.027 mmol) in 5 mL ethanol is added 5 mg of 10% Pd/C. The reaction mixture is treated with hydrogen at 1 atm pressure for 24 h, the solution filtered, and the product (20 mg, 90%) is obtained after removal of solvent.

EXAMPLE 15

Synthesis of amine-labelled $C_{60}$

Aminated $C_{60}$ is prepared in a method similar to that reported by Wudl et al. in "Fullerenes", pp 161–175, ACS Symposium Series 481 (1992). Ethylenediamine (20 mL, freshly distilled) is reacted with $C_{60}$ (15 mg, 0.022 mmol) at ambient temperature for 24 hrs with constant stirring. After two hours the originally green, paramagnetic solution (a doublet ESR signal was observed) turns brown and becomes diamagnetic. Addition of tetrahydrofuran (THF) precipitates the product, which is centrifuged, washed twice with THF and dried at ambient temperature in vacuo. The crude solid is dissolved in 2 mL of water, the insoluble material is separated by filtration, and addition of 20 mL of THF to the yellow solution precipitates the product. After centrifugation the yellow-brown powder is dried at ambient temperature in vacuo. The infra red spectrum (KBr pellet) shows absorbances at 3250 (m), 2980 (w), 2960 (w), 2940 (sh), 1450 (s, br), 1110 (s), 1020 (sh) and 860 (w) $cm^{-1}$. The FAB mass spectrum shows clusters of peaks centered at m/z 781 [$C_{60}(NH_2C_2H_4NH_2)$+H] and 720 ($C_{60}$). Titration of 1.4 mg of the product with 0.5M HCl shows two steps corresponding to the two amino groups per attached ethylenediamine unit. A total of 32 microliters of HCl is needed for the titration, corresponding to 12 amino groups per molecule, or an average stoichiometry of $C_{60}$ ($NH_2CH_2CH_2NH_2)_6$.

EXAMPLE 16

Fullerene derivative for use in photodynamic therapy

The cyclooctene complex (eta-5-$C_9H_7$) Ir(CO)(eta-2-$C_8H_{14}$), prepared as described by Szajek et al., Organometallics 10:357 (1991), (19 mg, 0.042 mmol) is reacted with 30 mg of $C_{60}$ (0.042 mmol) by heating in dichloromethane under reflux for 8 hr. The carbonyl stretch in the infrared spectrum of the Ir-containing starting material at 1954 $cm^{-1}$ is replaced by a single new carbonyl band at 1998 $cm^{-1}$. The solvent is evaporated and the black solid residue is washed with pentane and dried in vacuo. The yield is 25 mg (58%). Formulation of the product as (eta-5-$C_9H_7$)Ir(CO)($C_{60}$) is supported by microanalysis and mass spectrum (m/z 1059 for $^{193}$Ir). The resulting material is useful in generating singlet oxygen when irradiated with 388 nm light and is useful for the photodynamic therapy of cancer.

EXAMPLE 17

Synthesis of isotopically labelled fullerenes

Fullerenes are synthesized according to the method of Koch et al., J Org Chem 56:4543–4545 (1991) except that instead of using graphite having natural isotopic carbon abundance, graphite enriched in the carbon 13, carbon 14 or carbon 11 isotopes is employed as starting materials, thereby affording $C_{60}$ molecules enriched in either isotope. The carbon 13-enriched $C_{60}$ may be used as an in vivo magnetic resonance imaging agent, conveniently after appropriate derivatization, e.g. as described elsewhere herein. The carbon 11-enriched $C_{60}$ could be used as a PET agent, again optionally after derivatization. The carbon-14 enriched $C_{60}$ could be used as a source of countable radiation in a diagnostic test or in whole body autoradiography.

EXAMPLE 18

Synthesis of fluorinated fullerenes

Fluorinated fullerenes are prepared by treating brominated fullerenes with appropriate reagents. Thus $C_{60}Br_{24}$, prepared as described by Tebbe et al., Science, 256:822 (1992) is reacted with a suspension of potassium fluoride in sulfolane as described in J Chem Soc 6264 (1965) to afford a mixture of compounds having formulae $C_{60}Br_{24-x}F_x$ (where x=1, 2, 3, ...) as indicated by the mass spectrum of the resulting product mixture (m/e clusters being observed at 2638 ($C_{60}Br_{24}$ parent), 2577 ($C_{60}Br_{23}F$), 2516 ($C_{60}Br_{22}F_2$), etc.). Use of potassium fluoride labelled with the fluorine-18 isotope permits the synthesis of fluorine-18labelled brominated $C_{60}$ molecules Usable for PET imaging; use of commercially available potassium fluoride (consisting exclusively of fluorine isotope 19) affords materials that can be used for NMR imaging by monitoring the resonance of the $^{19}F$ nucleus.

EXAMPLE 19

Synthesis of mixed halogenated and hydroxylated fullerenes

Brominated fullerenes such as $C_{60}Br_{24}$ (see Example 18 above) are converted into mixed halogenated-hydroxylated fullerenes. For example, $C_{60}Br_{24}$ is refluxed with excess alcoholic KOH to afford a mixture of products having the general formula $C_{60}Br_{24-x}(OH)_x$ (where x=1, 2, 3, ...) as indicated by the mass spectrum of the resulting product mixture (m/e clusters observed at 2638 ($C_{60}Br_{24}$ parent), 2575 ($C_{60}Br_{23}(OH)$), 2514 ($C_{60}Br_{22}(OH)_2$), 2451 ($C_{60}Br_{21}(OH)_3$), etc). These mixed halogenated-hydroxylated fullerenes can be used as starting materials to make additional derivatized fullerene species using conventional techniques, i.e. the hydroxyl groups could be reacted with appropriate carboxylic acids to form substituted $C_{60}$ esters and with appropriate alcohols to form substituted $C_{60}$ ethers, for example.

EXAMPLE 20

Synthesis of Fullerene for Neutron Capture Therapy

To a solution of $C_{60}$ (15 mg, 0.022 mmol) in 25 mL of freshly-distilled (from $LiAlH_4$) tetrahydrofuran (THF) is added, dropwise with stirring, a solution of 1-Li-2-$CH_3$-$C_2B_{10}H_{10}$ in THF [prepared by reaction of 17.4 mg of $CH_3C_2B_{10}H_{11}$ with an equivalent amount of n-butyllithium (1.6M in hexane, Aldrich) in 10 mL THF]. The reaction mixture is stirred at ambient temperature for 1 hr, then any excess lithiated species is quenched with water, and the organic phase is separated and dried ($MgSO_4$). Mass spectrometry reveals the presence of a mixture of $C_{60}$ species labelled with carborane units, as shown by the present of m/e clusters centered at m/e 720 (parent $C_{60}$), 877 ($C_{60}C_2B_{10}H_3$), 1034 [$C_{60}(C_2B_{10}H_{10}CH_3)_2$], etc. These materials may be used in anticancer therapy using neutron irradiation.

EXAMPLE 21

Synthesis of fullerene useful for SPECT imaging

In a manner similar to that previously described, $In@C_{60}$ is prepared in which the indium is the 111 isotope by impregnating a graphite disk by exposure of it over a 24 hr period to a boiling aqueous solution of $^{111}InCl_3$. After rinsing and drying the disk is vaporized with a Nd:YAG laser and other apparatus described by Heath et al. (supra). The mass spectrum shows the presence of $^{111}In@C_{60}$ by a cluster of peaks centered at m/e 831. After separation, $^{111}In@C_{60}$ may be used as a contrast agent for SPECT imaging.

EXAMPLE 22

$C_{60}Br_{24}$

This was synthesized as described by Tebbe et al. in Science 256:822 (1992).

Measurements of $C_{60}$ and $C_{60}Br_{24}$ were performed using a Siemens Somatom DRG at 125 kV with 2.2 mm Al and 0.4 mm Cu filtering using 720 projections, 450 mAs, and a 4 mm slice thickness.

The samples were prepared by mixing the solids in gelatin as it was entering its gel phase. The samples were placed in a test tube (65 mm×13 mm) and then fastened in a PMMA holder. The test tubes were immersed in a water-containing plastic bowl having the dimensions 230 (W)×330 (L)×130 (D) mm. The bowl was placed on the patient-couch of the CT scanner.

The linear attenuation coefficients obtained for $C_{60}$ and $C_{60}Br_{24}$ were found to be 0.08 $cm^{-1}$ and 0.32 $cm^{-1}$, respectively.

The $C_{60}Br_{24}$ sample was found to be about a factor of 4 more attenuating than $C_{60}$ itself.

EXAMPLE 23

Cyclodextrin-$C_{60}$ inclusion complex

A: Incorporation of $C_{60}$ into γ-cyclodextrin

A procedure based on that of Andersson, et al. (J. Chem. Soc. Chem. Commun. 604–606 (1992)) was used:

(a) 2.59 mg, 2.0 mmol, of 7-cyclodextrin (Aldrich) was diluted to 100 mL with DI water (final concentration, 0.02 mmol). The solution was transferred to a 250 mL roundbottom flask equipped with reflux condenser.

(b) 11.7 mg, 16.2 μmol, of $C_{60}/C_{70}$ mixture buckminsterfullerene (2–12%, Johnson Mathey) was added and the mixture was refluxed for 24 h. At this time, a 5 mL aliquot was removed, filtered through 2 μm porosity paper and used for relaxivity measurements. The UV spectrum was obtained to confirm the presence of $C_{60}$ in the solution.

(c) The solution was refluxed for another day, total 48 h. A second 5 mL aliquot was then filtered and the UV spectrum was obtained to determine if the concentration of $C_{60}$ was increased with additional refluxing.

B: $C_{60}$ Control

A dark red solution of $C_{60}$ in toluene was prepared by dissolving 102.6 mg of $C_{60}$ in 50.00 mL of toluene at ambient temperature. The solution was free of visible solids. The final concentration was 2.052 mg/mL, 2.85 mM. (According to Sivaraman et al. (J. Org. Chem., 57:6077–6079 (1992)), the solubility of $C_{60}$ in toluene is 2.15 mg/mL at 30° C.: therefore the trial solution was probably nearly saturated in $C_{60}$).

C: UV Spectroscopy

The spectra of the $C_{60}$ loaded 7-cyclodextrin, a control γ-cyclodextrin (0.02 mM) and the $C_{60}$ in toluene solutions were obtained using a Cary 3 UV-Visible spectrometer. The γ-cyclodextrin solutions were scanned from 200 nm to 450 nm and, due to the background absorbance of toluene, the toluene solution was scanned from 300 nm to 800 nm.

D: NMR Relaxivity

T1 relaxation times were measured at 40° C. and 20 MHz on a Bruker Minispec PC 100 relaxometer. The pulse program (spin inversion) was used without modification. Measurements were made using the methodology recommended in the instrument manual. Measurements were carried out on 1.4 mL of each solution in a 10 mm NMR tube. The solutions used were: toluene; $C_{60}$ in toluene (2.85 mM);

0.02 mM γ-cyclodextrin in water; and $C_{60}$ in 0.02 mM γ-cyclodextrin in water.

E: Results

The UV spectra clearly showed that $C_{60}$ was extracted into aqueous γ-cyclodextrin: bands at 325 nm, 260 nm and 220 nm were found and the spectrum matched that obtained by Andersson et al. (supra). The 325 nm band was also seen in the $C_{60}$ toluene solution. Andersson et al. reported the maximum concentration obtained under similar experimental concentrations was 0.08 mM. A qualitative comparison of intensities of the 335 nm band in the toluene and aqueous γ-cyclodextrin trial solutions indicated a similar $C_{60}$ concentration.

Compared to the control solutions, pure toluene and 0.02 mM γ-cyclodextrin in water, the corresponding $C_{60}$ solutions were found to exhibit a reduction in the T1 relaxation times.

What is claimed is:

1. A compound comprising a curved or planar molecular mesh structure in the skeleton of which essentially all mesh aperture ring atoms are branching sites, said compound being externally linked to a metal or metal complex coordinating chelant group, or a conjugate, intercalate, inclusion compound or salt thereof, for use as a diagnostic or therapeutic agent.

2. A compound as claimed in claim 1 of formula I $$R_{2_n} @ R_{3_m} R_{4_{n'}} \quad (I)$$

where n and n' are zero or positive integers; m is an integer having a value of at least 20; $@R_{3_m}$ is a closed curved met-car, fullerene, faux fullerene or fulleroid formed from m mesh aperture ring atoms $R_3$ which may be the same or different; each $R_2$ which may be the same or different is a mono or polyatomic species entrapped within the $@R_{3_m}$ cage; and each $R_4$ which may be the same or different is a mono or polyatomic species covalently bound to the $@R_{3_m}$ cage) or a salt thereof.

3. A compound comprising a curved or planar molecular mesh structure in the skeleton of which essentially all mesh aperture ring atoms are branching sites, said compound being externally linked to a metal or metal complex coordinating chelant group, or a conjugate, intercalate, inclusion compound or salt thereof, for use as a diagnostic or therapeutic agent, said compound being of formula I $$R_{2_n} @ R_{3_m} R_{4_{n'}} \quad (I)$$

(where n and n' are zero or positive integers; m is an integer having a value of at least 20; $@R_{3_m}$ is a closed curbed met-car, fullerene, faux fullerene or fulleroid formed from m mesh aperture ring atoms $R_3$ which may be the same or different; each $R_2$ which may be the same or different is a mono or polyatomic species entrapped within the $@R_{3_m}$ cage; and each $R_4$ which may be the same or different is a mono or polyatomic species covalently bound to the $@R_3m$ cage) or a salt thereof, wherein at least one $R_2$ is present which is a transition or lanthanide metal and at least one $R_4$ is present which is a halogen atom.

4. A compound as claimed in claim 1 comprising a fullerene or fullerene derivative.

5. A compound as claimed in claim 4 comprising a $M_n @ C_m$ fullerene derivative (wherein n and m are positive integers and M is a metal) or a conjugate or salt thereof.

6. A compound as claimed in claim 5 wherein m is an even number 44 to 112, and n is 1, 2, 3 or 4.

7. A compounds as claimed in claim 6 wherein m is 60, 70, 80 or 82 and n is 1 or 2.

8. A compound as claimed in claim 5 wherein at least one M in $M_n @ C_m$ is paramagnetic.

9. A compound as claimed in claim 2 comprising a @ $C_m$ $Hal_{n'}$ fullerene halide (wherein m and n' are positive integers and Hal is F, Cl, Br or I) or a conjugate, inclusion compound or salt thereof.

10. A compound comprising a curved or planar molecular mesh structure in the skeleton of which essentially all mesh aperture ring atoms are branching sites, said compound being externally linked to a metal or metal complex coordinating chelant group, or a conjugate, intercalate, inclusion compound or salt thereof, for use as a diagnostic or therapeutic agent, comprising a metallo-carbohedrane or a derivative thereof.

11. A compound as claimed in claim 10 comprising a $@M'_{m_1}C_{m_2}$ metallo-carbohedrane (wherein M' is a transition metal and $m_1$ and $m_2$ are positive integers) or a derivative thereof.

12. A compound comprising a curved or planar molecular mesh structure in the skeleton of which essentially all mesh aperture ring atoms are branching sites, said compound being externally linked to a metal or metal complex coordinating chelant group, or a conjugate, intercalate, inclusion compound or salt thereof, for use as a diagnostic or therapeutic agent, comprising a Gd encapsulating molecular mesh structure.

13. A compound as claimed in claim 1 being a dendrimeric compound of formula II $$(Fu)_x(L)_y \quad (II)$$

where each Fu is a moiety of formula Ia $$R_{2_n} @ R_{3_m} R'_{4_{n'}} \quad (Ia)$$

where each $R_2$ which may be the same or different is a mono or polyatomic species entrapped within the $@R_{3_m}$ cage; $@R_{3_m}$ is a closed curved met-car, fullerene, faux fullerene or fulleroid formed from m mesh aperture ring atoms $R_3$ which may be the same or different, n and n' are zero or positive integers, m is an integer having a value or at least 20, and each $R'_4$ which may be the same or different is a mono or polyatomic species covalently bound to the $@R_{3_m}$ cage or is a bond to an L moiety linked to at least one linker moiety L; and x and y are integers each having a value of 1 to 100.

14. A compound comprising a curved or planar molecular mesh structure in the skeleton of which essentially all mesh aperture ring atoms are branching sites, said compound being externally linked to a metal or metal complex coordinating chelant group, or a conjugate, intercalate, inclusion compound or salt thereof, for use as a diagnostic or therapeutic agent, comprising at least one curved molecular mesh structure linked to a metal or metal complex coordinating chelant group.

15. A compound as claimed in claim 14 comprising at least one metal complex coordinating chelant group wherein the chelated complex comprises at least two metal atoms.

16. A compound as claimed in claim 12 being $Gd_n @ C_m$ (where n and m are positive integers) optionally water-solubilized by derivatisation or carrier enclosure.

17. A compound comprising a curved or planar molecular mesh structure in the skeleton of which essentially all mesh aperture ring atoms are branching sites, said compound being externally linked to a metal or metal complex coordinating chelant group, or a conjugate, intercalate, inclusion compound or salt thereof, for use as a diagnostic imaging contrast agent.

18. A diagnostic composition comprising a sterile pharmaceutically acceptable carrier or excipient together with an image contrast enhancing physiologically tolerable compound comprising a curved or planar molecular mesh structure in the skeleton of which essentially all mesh aperture ring atoms are branching sites, said compound being externally linked to a metal or metal complex coordinating chelant group, or a conjugate, intercalate, inclusion compound or salt thereof.

19. A composition as claimed in claim 18 wherein said compound contains a diagnostically effective moiety.

20. A composition as claimed in claim 19 wherein said moiety is enclosed by said molecular mesh structure.

21. A composition as claimed in claim 19 wherein said moiety is attached to said molecular mesh structure.

22. A composition as claimed in claim 19 wherein said moiety forms part of the skeleton of said molecular mesh structure.

23. A composition as claimed in claim 19 wherein said moiety is selected from radiolabels, magnetic labels, elements of atomic number greater than 50, chromophores and fluorophores.

24. A composition as claims in claim 18 wherein said compound is

$$R_{2_n}@R_{3_m}R_{4_{n'}} \quad (I)$$

where n and n' are zero or positive integers; m is an integer having a value of at least 20: $@R_{3_m}$ is a closed curved met-car, fullerene, faux fullerene or fulleroid formed from m mesh aperture ring atoms $R_3$ which may be the same or different; each $R_2$ which may be the same or different is a mono or polyatomic species entrapped within the $@R_{3_m}$ cage; and each $R_4$ which may be the same or different is a mono or polyatomic species covalently bound to the $@R_{3_m}$ cage) or a salt thereof.

25. A pharmaceutical composition comprising a sterile pharmaceutically acceptable carrier or excipient together with a therapeutically effective compound comprising a curved molecular mesh structure in the skeleton of which essentially all mesh aperture ring atoms are branching sites, said compound being externally linked to a metal or metal complex coordinating chelant group, or a conjugate, intercalate, inclusion compound or salt thereof.

26. A composition comprising a sterile pharmaceutically acceptable carrier or excipient together with a therapeutically effective compound comprising a curved molecular mesh structure in the skeleton of which essentially all mesh aperture ring atoms are branching sites, said compound being externally linked to a metal or metal complex coordinating chelant group, or a conjugate, intercalate, inclusion compound or salt thereof wherein said compound contains a therapeutically effective metal.

27. A composition as claimed in claim 25 wherein said compound contains a therapeutically active entity releasably conjugated to said molecular mesh structure.

28. A composition as claimed in claim 25 wherein said compound comprises a photo-activatable therapeutic entity.

29. A method of imaging of a subject comprising: introducing into said subject a compound comprising a curved or planar molecular mesh structure in the skeleton or which essentially all mesh aperture ring atoms are branching sites, said compound being externally linked to a metal or metal complex coordinating chelant group, or a conjugate, intercalate, inclusion compound or salt thereof, which compound contains a moiety capable of modifying image contrast in an imaging modality; and generating an image of at least part of said subject by said imaging modality.

30. A method as claimed in claim 29 wherein said moiety is a metal having a non-zero magnetic moment and said modality is magnetic resonance imaging or magnetometric imaging.

31. A method as claimed in claim 29 wherein said moiety is an element having an atomic number greater than 50 and said modality is X-ray CT.

32. A method as claimed in claim 29 wherein said modality is EIT, infra-red imaging, ultrasound, PET, or SPECT.

33. A method of treatment of a condition responsive to radiotherapy or metal ion therapy, said method comprising administering to a subject a therapeutically effective amount of physiologically tolerable compound comprising a curved or planar molecular mesh structure in the skeleton of which essentially all ring atoms are branching sites, said compound being externally linked to a metal or metal complex coordinating chelant group, said compound comprising at least one atom of a therapeutically effective metal or radioisotope.

34. A medical apparatus characterized in that at least a portion of the apparatus incorporates or is coated with a curved molecular mesh structure compound comprising a diagnostically or therapeutically effective entity and in the mesh skeleton of which essentially all mesh aperture ring atoms are branching sites, said compound being externally linked to a metal or metal complex coordinating chelant group, or a conjugate, intercalate, inclusion compound or salt thereof.

35. Apparatus as claimed in claim 34 wherein said diagnostically or therapeutically effective entity is selected from radiolabels, magnetic labels, elements of atomic number greater than 50, chromophores, fluorophores and singlet oxygen generators.

* * * * *